United States Patent
Morita et al.

(10) Patent No.: US 9,833,426 B2
(45) Date of Patent: Dec. 5, 2017

(54) AGENT FOR PREVENTING DETERIORATION IN VASCULAR ENDOTHELIAL FUNCTION OR IMPROVING VASCULAR ENDOTHELIAL FUNCTION

(71) Applicant: KYOWA HAKKO BIO CO., LTD., Tokyo (JP)

(72) Inventors: Masahiko Morita, Tsukuba (JP); Miho Yin Komatsu, Tsukuba (JP); Takahiro Hara, Tsukuba (JP)

(73) Assignee: Kyowa Hakko Bio Co., Ltd., Tokyo (JP)

(*) Notice: Subject to any disclaimer, the term of this patent is extended or adjusted under 35 U.S.C. 154(b) by 0 days.

(21) Appl. No.: 14/411,169

(22) PCT Filed: Jun. 28, 2013

(86) PCT No.: PCT/JP2013/067767
§ 371 (c)(1),
(2) Date: Dec. 24, 2014

(87) PCT Pub. No.: WO2014/003154
PCT Pub. Date: Jan. 3, 2014

(65) Prior Publication Data
US 2015/0141514 A1   May 21, 2015

(30) Foreign Application Priority Data
Jun. 29, 2012   (JP) .................................. 2012-146572

(51) Int. Cl.
A01N 37/12 (2006.01)
A01N 37/44 (2006.01)
A61K 31/195 (2006.01)
A61K 31/198 (2006.01)

(52) U.S. Cl.
CPC .................................. *A61K 31/198* (2013.01)

(58) Field of Classification Search
None
See application file for complete search history.

(56) References Cited

U.S. PATENT DOCUMENTS

| 2002/0143060 A1 | 10/2002 | Kohchi et al. |
| 2005/0075401 A1 | 4/2005 | Kohchi et al. |
| 2007/0191485 A1 | 8/2007 | Kohchi et al. |
| 2010/0004335 A1* | 1/2010 | Kagami ............... A61K 8/02 514/563 |

FOREIGN PATENT DOCUMENTS

| JP | H09-110686 A | 4/1997 |
| JP | 2002-226370 A | 8/2002 |
| JP | 2002-316929 A | 10/2002 |
| JP | 2006-282648 A | 10/2006 |
| JP | 2006282648 A * | 10/2006 |
| JP | 2008-222632 A | 9/2008 |
| JP | 2008-273910 A | 11/2008 |
| JP | 2008273910 A * | 11/2008 |
| WO | WO 2007/066642 A1 | 6/2007 |

OTHER PUBLICATIONS

Furuse et al., Proceedings of Japanese Society of Japanese Society for Animal Nutrition and Metabolism, 52(2): 31-41 (Oct. 15, 2008).
Hayashi et al., *Proc. Natl. Acad. of Sciences*, 102(38): 13681-13686 (Sep. 20, 2005).
Mishra et al., *Am. J. Physiology Heart Circ. Physiology*, 298: H1789-H1796 (2010).
Morita et al., *Folia Pharmacol. Jpn.* 136: 185 (2010).
Morita et al., *The Japanese Society of Nutrition and Food Science Taikai Koen Yoshishu*, p. 243, entry 3N-07p (May 1, 2010).
Morita et al., *The Japanese Journal of Surgical Metabolism and Nutrition*, 44(3): 76, entry P-07 (Jun. 2010).
Morita et al., *Dai 63 Kai The Japanese Society of Nutrition and Food Science Taikai Koen Yoshishu*, p. 155, entry 2M-09a (Apr. 25, 2011).
Narita et al., *Abstracts of 130th Annual Meeting of Pharmaceutical Society of Japan* 2, p. 237, entry 29p-pm205 (Mar. 5, 2010).
Japanese Patent Office, International Search Report in International Patent Application No. PCT/JP2013/067767 (dated Sep. 17, 2013).

* cited by examiner

*Primary Examiner* — Dennis Heyer
*Assistant Examiner* — Daniel M Podgorski
(74) *Attorney, Agent, or Firm* — Leydig, Voit & Mayer, Ltd.

(57) ABSTRACT

An agent for enhancing NO production, comprising citrulline or a salt thereof and serine or a salt thereof as an active ingredient. An agent for preventing or ameliorating vascular endothelial malfunction, comprising citrulline or a salt thereof and serine or a salt thereof as an active ingredient. An agent for preventing or ameliorating a symptom caused by vascular endothelial malfunction, comprising citrulline or a salt thereof and serine or a salt thereof as an active ingredient.

18 Claims, 2 Drawing Sheets

AGENT FOR PREVENTING DETERIORATION IN VASCULAR ENDOTHELIAL FUNCTION OR IMPROVING VASCULAR ENDOTHELIAL FUNCTION

CROSS-REFERENCE TO RELATED APPLICATIONS

This patent application is the U.S. national phase of International Patent Application No. PCT/JP2013/067767, filed Jun. 28, 2013, which claims the benefit of Japanese Patent Application No. 2012-146572, filed on Jun. 29, 2012, which are incorporated by reference in their entireties herein.

TECHNICAL FIELD

The present invention relates to an agent for preventing or ameliorating vascular endothelial malfunction which comprises citrulline or a salt thereof and serine or a salt thereof as an active ingredient and has a higher effect of enhancing nitrogen monoxide (NO) production.

BACKGROUND ART

Citrulline is a type of amino acids existing in a free state and is not used as a substance of protein synthesis in the body. This compound plays an important role as an arginine precursor in arginine biosynthesis and as a constituting factor of NO cycle associated with NO supply in the body. NO produced by vascular endothelial cells exhibits a wide range of physiological activities for maintaining normal blood vessel functions such as vascular relaxation, LDL oxidation inhibition, platelet aggregation inhibition, smooth muscle cell antiproliferation, and anti-oxidation. Arteriosclerosis is a symptom that involves loss of elasticity of the vascular wall due to increased inflammatory response in vascular intima and cholesterol accumulation. Such a symptom makes it difficult to maintain a smooth blood flow and promotes formation of blood clots. Many studies indicate a decrease in NO produced by vascular endothelial cells as a cause of this symptom. That is, it can be expected that enhancement of NO production in vascular endothelial cells prevents or ameliorates arteriosclerosis and other ischemic vascular diseases caused by vascular endothelial malfunction and promotes blood flow.

It is reported that citrulline ingestion has an anti-arteriosclerosis effect and a blood flow ameliorating effect mediated by the production of NO which is a vasodilatation factor (Non-Patent Document 1) and citrulline has been used mainly in the United States as a food material for producing NO to ameliorate blood flow. In Europe, citrulline is used as an anti-fatigue drug in the form of citrulline malate.

Serine is one of the nonessential amino acids and plays an important role in a biological function as a constituent element of protein, particularly by existing in the active center of an enzyme. Further, serine is known as a component whose content is the largest among the amino acids contained in natural moisturizing factors for constantly maintaining the water content in the skin.

Heretofore, it has been found that oral administration of serine to mice in which chronic rheumatoid arthritis was induced has an effect of ameliorating the arthritis score (Patent Document 1). Further, it is reported that, the average blood pressure was decreased and the peripheral vascular resistance was decreased in a transient manner (Non-Patent Document 2) by intravenous acute administration of serine to normal rats and spontaneously hypertensive rats (SHR). A study using an NO synthase inhibitor and a calcium-dependent potassium channel inhibitor has revealed that this effect occurs independently of NO by relaxation of vascular smooth muscle through the activation of calcium-dependent potassium channels.

As described above, it has not been known that serine has an effect of promoting NO production and that a synergistic effect of enhancing NO production can be obtained by combining serine and a salt thereof with citrulline or a salt thereof.

PRIOR ART

Patent Document

Patent Document 1: JP-A-2008-222632

Non-Patent Document

Non-Patent Document 1: PNAS, 2005, Vol. 102, pp. 13681-13686
Non-Patent Document 2: American Journal of Physiology, Heart and Circulatory Physiology, 2010, Vol. 298, pp. 1789-1796

SUMMARY OF INVENTION

Problems to be Solved by the Invention

An object of the present invention is to provide an agent for preventing or ameliorating a vascular endothelial malfunction and an arteriosclerosis-related symptom caused by the progress of vascular endothelial malfunction (e.g., an ischemic disease such as cerebral infarction, myocardial infarction, angina, peripheral artery occlusion, pulmonary hypertension, or renal dysfunction) or a decrease in a blood flow-related symptom (e.g., stiff shoulders, excessive sensitivity to cold, swelling, erectile dysfunction, rough skin, a memory and learning disorder, a decrease in attention concentration, and a decrease in exercise performance due to decreased skeletal muscle activity), which has a higher effect of enhancing NO production.

Means for Solving the Problems

The present invention relates to the following (1) to (32):
(1) An agent for enhancing NO production, comprising citrulline or a salt thereof and serine or a salt thereof as an active ingredient.
(2) An agent for preventing or ameliorating vascular endothelial malfunction, comprising citrulline or a salt thereof and serine or a salt thereof as an active ingredient.
(3) An agent for preventing or ameliorating a symptom caused by vascular endothelial malfunction, comprising citrulline or a salt thereof and serine or a salt thereof as an active ingredient.
(4) The agent for prevention or amelioration according to (3), wherein the symptom caused by vascular endothelial malfunction is an arteriosclerosis-related symptom or a decrease in a blood flow-related symptom.
(5) The agent for prevention or amelioration according to (4), wherein the arteriosclerosis-related symptom is an ischemic disease.
(6) The agent for prevention or amelioration according to (5), wherein the ischemic disease is at least one symptom selected from cerebral infarction, myocardial infarction, angina, peripheral artery occlusion, pulmonary hypertension, and renal dysfunction.

(7) The agent for prevention or amelioration according to (4), wherein the decrease in a blood flow-related symptom is at least one symptom selected from stiff shoulders, excessive sensitivity to cold, swelling, erectile dysfunction, rough skin, a memory and learning disorder, a decrease in attention concentration, and a decrease in exercise performance due to decreased skeletal muscle activity.

(8) A method for preventing or ameliorating vascular endothelial malfunction, characterized by oral ingestion of citrulline or a salt thereof and serine or a salt thereof as an active ingredient.

(9) A method for preventing or ameliorating vascular endothelial malfunction, characterized by ingestion of an oral agent comprising citrulline or a salt thereof and serine or a salt thereof as an active ingredient.

(10) A method for preventing or ameliorating vascular endothelial malfunction, characterized by oral ingestion of citrulline or a salt thereof and serine or a salt thereof as an active ingredient, provided that the method for prevention or amelioration does not include any medical practice to human.

(11) A method for preventing or ameliorating vascular endothelial malfunction, characterized by ingestion of an oral agent comprising citrulline or a salt thereof and serine or a salt thereof as an active ingredient, provided that the method for prevention or amelioration does not include any medical practice to human.

(12) A method for enhancing NO production, comprising a step of administering effective an amount of citrulline or a salt thereof and serine or a salt thereof.

(13) A method for preventing or ameliorating vascular endothelial malfunction, comprising a step of administering an effective amount of citrulline or a salt thereof and serine or a salt thereof.

(14) A method for preventing or ameliorating a symptom caused by vascular endothelial malfunction, comprising a step of administering an effective amount of citrulline or a salt thereof and serine or a salt thereof.

(15) The method for prevention or amelioration according to (14), wherein the symptom caused by vascular endothelial malfunction is an arteriosclerosis-related symptom or a decrease in a blood flow-related symptom.

(16) The method for prevention or amelioration according to (15), wherein the arteriosclerosis-related symptom is an ischemic disease.

(17) The method for prevention or amelioration according to (16), wherein the ischemic disease is at least one symptom selected from cerebral infarction, myocardial infarction, angina, peripheral artery occlusion, pulmonary hypertension, and renal dysfunction.

(18) The method for prevention or amelioration according to (15), wherein the decrease in a blood flow-related symptom is at least one symptom selected from stiff shoulders, excessive sensitivity to cold, swelling, erectile dysfunction, rough skin, a memory and learning disorder, a decrease in attention concentration, and a decrease in exercise performance due to decreased skeletal muscle activity.

(19) Use of citrulline or a salt thereof and serine or a salt thereof for the manufacture of an agent for enhancing NO production.

(20) Use of citrulline or a salt thereof and serine or a salt thereof for the manufacture of an agent for preventing or ameliorating vascular endothelial malfunction.

(21) Use of citrulline or a salt thereof and serine or a salt thereof for the manufacture of an agent for preventing or ameliorating a symptom caused by vascular endothelial malfunction.

(22) The use according to (21), wherein the symptom caused by vascular endothelial malfunction is an arteriosclerosis-related symptom or a decrease in a blood flow-related symptom.

(23) The use according to (22), wherein the arteriosclerosis-related symptom is an ischemic disease.

(24) The use according to (23), wherein the ischemic disease is at least one symptom selected from cerebral infarction, myocardial infarction, angina, peripheral artery occlusion, pulmonary hypertension, and renal dysfunction.

(25) The use according to (22), wherein the decrease in a blood flow-related symptom is at least one symptom selected from stiff shoulders, excessive sensitivity to cold, swelling, erectile dysfunction, rough skin, a memory and learning disorder, a decrease in attention concentration, and a decrease in exercise performance due to decreased skeletal muscle activity.

(26) Citrulline or a salt thereof and serine or a salt thereof for use in enhancing NO production.

(27) Citrulline or a salt thereof and serine or a salt thereof for use in preventing or ameliorating vascular endothelial malfunction.

(28) Citrulline or a salt thereof and serine or a salt thereof for use in preventing or ameliorating a symptom caused by vascular endothelial malfunction.

(29) The citrulline or a salt thereof and serine or a salt thereof according to (28), wherein the symptom caused by vascular endothelial malfunction is an arteriosclerosis-related symptom or a decrease in a blood flow-related symptom.

(30) The citrulline or a salt thereof and serine or a salt thereof according to (29), wherein the arteriosclerosis-related symptom is an ischemic disease.

(31) The citrulline or a salt thereof and serine or a salt thereof according to (30), wherein the ischemic disease is at least one symptom selected from cerebral infarction, myocardial infarction, angina, peripheral artery occlusion, pulmonary hypertension, and renal dysfunction.

(32) The citrulline or a salt thereof and serine or a salt thereof according to (29), wherein the decrease in a blood flow-related symptom is at least one symptom selected from stiff shoulders, excessive sensitivity to cold, swelling, erectile dysfunction, rough skin, a memory and learning disorder, a decrease in attention concentration, and a decrease in exercise performance due to decreased skeletal muscle activity.

Effects of the Invention

According to the present invention, an agent for preventing or ameliorating vascular endothelial malfunction which comprises citrulline or a salt thereof and serine or a salt thereof as an active ingredient, is safe and effective, and has a higher effect of enhancing NO production can be provided.

Figure 2:
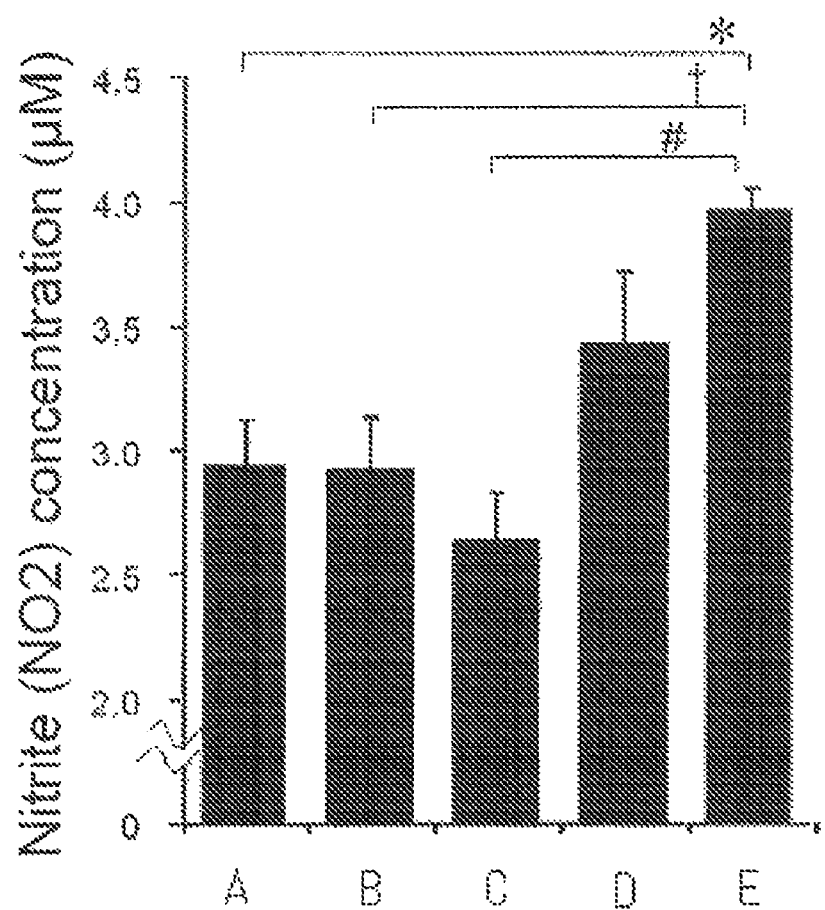

FIG. 2 represents the concentration of nitrite ($NO_2$) which is a stable NO metabolite in media after adding the sample at each concentration to HUVEC. In the figure, A represents a control group, B represents a low-dose citrulline-added group (0.3 mM), C represents a serine-added group (0.3 mM), D represents a high-dose citrulline-added group (3 mM), and E represents a high-dose citrulline and serine-added group. The data are expressed as mean±SEM (standard error), and N=3. Further, * indicates that there is a significant difference ($P<0.05$) in the high-dose citrulline and serine-added group as compared with the control group, † indicates that there is a significant difference ($P<0.05$) in the high-dose citrulline and serine-added group as compared with the low-dose citrulline-added group, and # indicates that there is a significant difference ($P<0.05$) in the high-dose citrulline and serine-added group as compared with the serine-added group.

DETAILED DESCRIPTION OF THE INVENTION

Examples of citrulline used in the present invention include L-citrulline and D-citrulline, preferably L-citrulline. Citrulline can be obtained by a chemical synthesis method, a fermentation production method, and the like. Citrulline can also be obtained by purchasing a commercially available product. Examples of the chemical synthesis method for citrulline include the methods described in J. Biol. Chem., 122, 477 (1938) and J. Org. Chem., 6, 410 (1941).

Examples of the fermentation production method for L-citrulline include the methods described in JP-A-1978-075387 and JP-A-1988-068091. L-Citrulline and D-citrulline can also be purchased from Sigma-Aldrich and the like.

Examples of the citrulline salt include an acid addition salt, a metal salt, an ammonium salts, an organic amine addition salt, an amino acid addition salt and the like. Examples of the acid addition salt include an inorganic acid salt such as hydrochlorides, sulfate, nitrate, and phosphate, and an organic acid salt, such as acetate, maleate, fumarate, citrate, malate, lactate, α-ketoglutarate, gluconate, or caprylate.

Examples of the metal salt include alkali metal salt, such as sodium salts or a potassium salt, an alkaline earth metal salt, such as a magnesium salt or a calcium salt, an aluminum salt, and a zinc salt, and the like.

Examples of the ammonium salt include an ammonium salt, a tetramethylammonium salt, and the like.

Examples of the organic amine addition salt include a morpholine salt, a piperidine salt, and the like.

Examples of the amino acid addition salt include salts of glycine, phenylalanine, lysine, aspartic acid, glutamic acid, and the like. Among the above salts of citrulline, a malate is preferably used. However, another salt, or two or more combinations of the above salts may be optionally used.

Examples of serine used in the present invention include L-serine and D-serine.

L-serine and D-serine used in the present invention may be obtained by any process. Examples of the production method for L-serine and D-serine include a fermentation method using a microorganism, a chemical synthesis method, an enzymatic method, and the like. L-serine and D-serine can also be obtained by purchasing commercially available products. For example, L-serine and D-serine can also be purchased from Sigma-Aldrich and the like.

L-serine and D-serine contained in the agent for preventing or ameliorating vascular endothelial malfunction of the present invention may exist therein in the form of a salt thereof. Examples of the L-serine and D-serine salt include the same as those described in the salt of citrulline.

In the present invention, a substance involved in the synthesis of serine in the body, for example, phosphoserine, glutamic acid, and the like can also be used instead of serine.

The composition ratio of citrulline or a salt thereof and serine or a salt thereof contained in the agent for preventing or ameliorating vascular endothelial malfunction of the present invention is 1:100 to 100:1, preferably 1:50 to 50:1, particularly preferably 10:1 to 1:10 in weight ratio.

As the agent for preventing or ameliorating vascular endothelial malfunction of the present invention, citrulline or a salt thereof and serine or a salt thereof can be ingested or administered as such. However, it is generally preferred to provide the agent as various kinds of production forms or preparations.

The product or preparation contains citrulline or a salt thereof and serine or a salt thereof as an active ingredient. However, the product or preparation may further contain any other active ingredients. The product or preparation is produced by mixing the active ingredient with one or more pharmaceutically acceptable carriers using any methods well known in the technical field of pharmaceuticals.

It is desirable to ingest or administer the product or preparation in the form that is the most effective for preventing or ameliorating vascular endothelial malfunction.

Examples of the ingestion or administration form of the product or preparation include oral ingestion or administration; parenteral administration, such as intravenous, intraperitoneal, or subcutaneous administration. Preferred is oral ingestion or administration.

Form or dosage form of the ingestion or administration may be an oral preparation such as a tablet, a powder, a granule, a pill, a suspension, an emulsion, an infusion/decoction, a capsule, a drink, a liquid, an elixir, an extract, a tincture, or a fluidextract, or a parenteral preparation such as an injection, a drop, a cream, or a suppository. Preferred is an oral preparation.

Liquid preparations suitable for ingestion or oral administration such as a drink can be prepared by adding water, a sugar such as sucrose, sorbitol, or fructose, a glycol such as polyethylene glycol or propylene glycol, an oil such as sesame oil, olive oil, or soybean oil, an antiseptic such as a p-hydroxybenzoic acid ester, a preservative such as a paraoxybenzoic acid derivative such as methyl paraoxybenzoate, or sodium benzoate, a flavor such as a strawberry or peppermint flavor.

Tablets, powders, and granules suitable for oral ingestion or administration may be prepared by adding excipient such as a sugar (such as lactose, white soft sugar, glucose, sucrose, mannitol, or sorbitol), starch (such as potato, wheat, or corn), an inorganic substance (such as calcium carbonate, calcium sulfate, sodium hydrogen carbonate, or sodium chloride), crystalline cellulose, or a plant powder (such as licorice powder or gentian powder); a disintegrant (such as starch, agar, gelatin powder, crystalline cellulose, carmellose sodium, carmellose calcium, calcium carbonate, sodium hydrogencarbonate, or sodium alginate); a lubricant (such as magnesium stearate, talc, hydrogenated vegetable oil, Macrogol, or silicone oil); a binder (such as polyvinyl alcohol, hydroxypropyl cellulose, methyl cellulose, ethyl cellulose, carmellose, gelatin, or starch paste); a surfactant (such as fatty acid ester); a plasticizer (such as glycerin), or the like.

The production form or preparation suitable for oral ingestion or administration may also contain an additive generally used in foods and drinks, such as a sweetener, a color, a preservative, a thickening stabilizer, an antioxidant, a color former, a bleaching agent, an anti-fungal agent, a gum base, a bittering agent, an enzyme, a brightening agent, an acidulant, a flavor enhancer, an emulsifier, a toughening agent, a production agent, a flavor, or a spice extract.

The product form or preparation suitable for oral ingestion or administration can be processed and produced into a tablet, a powder, a granule, a pill, a suspension, an emulsion, an infusion/decoction, a capsule, a drink, a liquid, an elixir, an extract, a tincture, or a fluidextract in a unit packaged form per ingestion depending on, for example, the ingestion duration, ingestion frequency, ingestion amount, or the like. For example, the "unit packaged form per one ingestion" is a form in which the amount of ingestion per dose is predetermined, and the "unit packaged form per one week to three months" is a form in which the amount to be ingested for one week to three months is included. Examples of the unit packaged form include a form in which a given amount is specified with a pack, a packaging, a bottle, or the like.

In the case where the product form or preparation is a drink, examples of the "unit packaged form per one ingestion" include a form in which a drink obtained by suspending or dissolving 50 mg or more of citrulline or a salt thereof and serine or a salt thereof is placed in a bottle and the like in such a form that all the content therein should be taken at one time per one ingestion.

In the case where the ingestion frequency is once daily and the daily ingestion amount is 300 mg, and a tablet contains 50 mg of citrulline or a salt thereof and serine or a salt thereof, examples of the "unit packaged form per one week to three months" include a form in which 42 to 540 tablets are packaged.

The preparation suitable for parenteral administration such as an injection preferably comprises a sterile aqueous agent which contains citrulline or a salt thereof and serine or a salt thereof, and is isotonic to the recipient's blood. For example, in the case of an injection, an injectable solution is prepared by using a carrier consisting of a salt solution, a glucose solution, or a mixture of a salt solution and a glucose solution, and the like.

Also to such a parenteral preparation, one or more auxiliary components selected from an antiseptic, a preservative, an excipient, a disintegrant, a lubricant, a binder, a surfactant, a plasticizer, and the like as described in the oral preparation can be added.

The concentration of the citrulline or a salt thereof and serine or a salt thereof in the agent for preventing or ameliorating vascular endothelial malfunction of the present invention is appropriately determined according to the type of product forms or preparations, the expected effect by the ingestion or administration of the product or preparation, and the like. However, the concentration of citrulline or a salt thereof is typically 0.1 to 100% by weight, preferably 0.5 to 80% by weight, and particularly preferably 1 to 70% by weight.

The ingestion amount or dose and the ingestion or dosing frequency of the agent for preventing or ameliorating vascular endothelial malfunction of the present invention depend on the ingestion or dosage form, the age and body weight of an subject in need of ingestion or administration, and the nature or seriousness of the symptom to be treated. In general, the agent is given in a daily dose of 50 mg to 30 g, preferably 100 mg to 10 g, particularly preferably 200 mg to 3 g for an adult in terms of citrulline or a salt thereof and serine or a salt thereof, once to several times a day.

The duration of ingestion or administration is not particularly limited. However, it is generally 1 day to 1 year, preferably 1 week to 3 months.

The agent for preventing or ameliorating vascular endothelial malfunction of the present invention can be used for the NO production-mediated prevention or amelioration of vascular endothelial malfunction. The agent for preventing or ameliorating vascular endothelial malfunction of the present invention can be used for the prevention or amelioration of an arteriosclerosis-related symptom caused by the progress of vascular endothelial malfunction or for the prevention or amelioration of a decrease in a blood flow-related symptom. Examples of the effect expected from the prevention or amelioration of an arteriosclerosis-related symptom caused by the progress of vascular endothelial malfunction include prevention or amelioration of an ischemic disease such as cerebral infarction, myocardial infarction, angina, peripheral artery occlusion, pulmonary hypertension, or renal dysfunction. Examples of the effect expected from the prevention or amelioration of a decrease in a blood flow-related symptom include prevention or amelioration of stiff shoulders, excessive sensitivity to cold, swelling, erectile dysfunction, rough skin, a memory and learning disorder, a decrease in attention concentration, and a decrease in exercise performance due to decreased skeletal muscle activity.

Accordingly, by allowing a subject who wants to prevent the occurrence of such a symptom or presents such a symptom to ingest the agent for preventing or ameliorating vascular endothelial malfunction of the present invention or by administering the agent to the subject, such a symptom can be prevented or ameliorated.

In addition, in the present invention, citrulline or a salt thereof and serine or a salt thereof can be used for the manufacture of the agent for preventing or ameliorating vascular endothelial malfunction.

Further, the present invention also includes a method for elevating NO. The method of the present invention includes a step of allowing a subject in need of NO elevation to ingest citrulline or a salt thereof and serine or a salt thereof or administering citrulline or a salt thereof and serine or a salt thereof to the subject in a sufficient amount for elevating the NO level of the subject.

Still further, the present invention also includes a method for preventing or ameliorating vascular endothelial malfunction. The method of the present invention includes a step of allowing a subject in need of prevention or amelioration of vascular endothelial malfunction to ingest citrulline or a salt thereof and serine or a salt thereof or administering citrulline or a salt thereof and serine or a salt thereof to the subject in a sufficient amount for preventing or ameliorating vascular endothelial malfunction of the subject.

The following describes a test example concerning the effects of citrulline and serine on NO production.

Test Example

A normal human umbilical vein endothelial cells (HUVEC) line available from Clonetics (SanDiego, Calif., USA) was used with EGM-2 Bullet Kit medium containing 2% FBS (Takara Bio Inc.). The cells were cultured at 37° C. in a 5% $CO_2$ incubator, and used for experiments after 4 to 6 passages. Citrulline and serine, which were manufactured by Kyowa Hakko Bio, were used.

A cell suspension (0.45 mL) with the adjusted initial cell density to $1\times10^5$ cells/mL was inoculated in a 24-well plate (IWAKI). After 24-hour culture, the medium was replaced with a medium containing L-citrulline (final concentration 0.3 mM: low-dose citrulline group, or final concentration 3 mM: high-dose citrulline group), L-serine (final concentration 0.3 mM: serine group), or a mixture thereof (citrulline final concentration 0.3 mM and serine final concentration 0.3 mM: low-dose citrulline+serine group, or citrulline final concentration 3 mM and serine final concentration 0.3 mM: high-dose citrulline+serine group). In a control group, a medium to which only a solvent (PBS) was added was used. After 48-hour culture, the culture broth (100 L) was centrifuged at 12,000 rpm for 10 minutes, and the concentration of nitrite ($NO_2$), which is a stable NO metabolite, in the culture supernatant was determined by HPLC (ENO-20, EICOM).

Further, we confirmed that the cell viability was not affected in all of the addition groups in this test in MTT assay.

Figure 1:
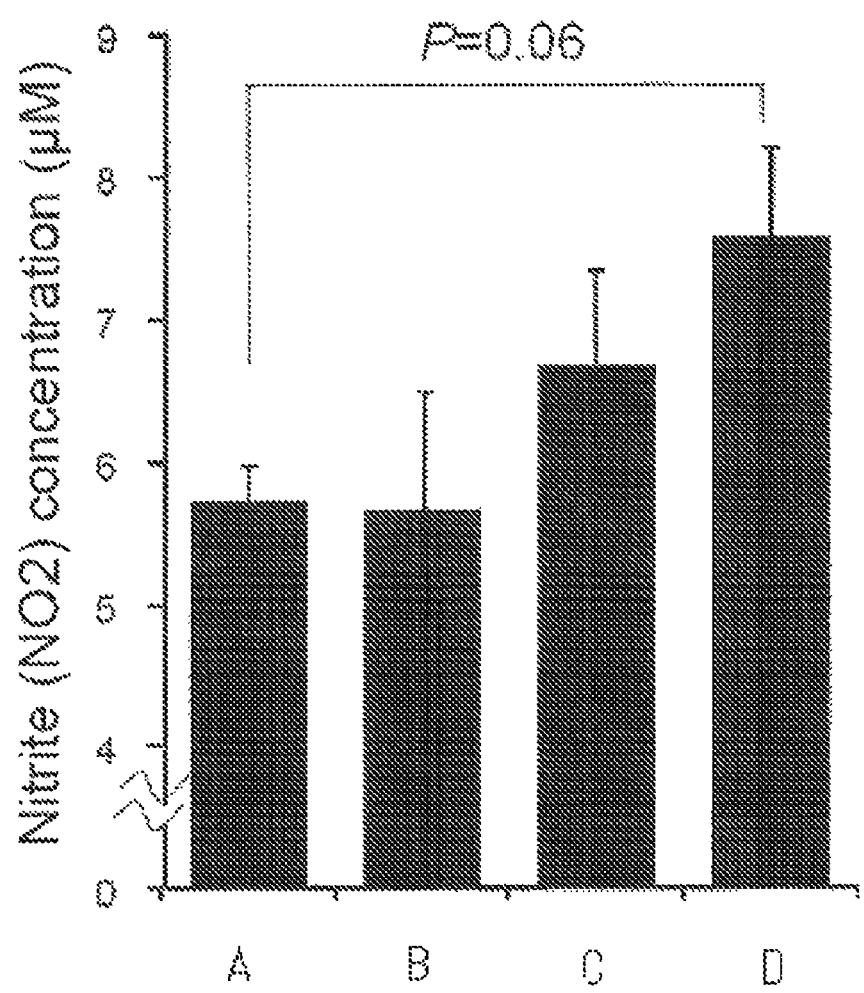
FIG. 1 represents the concentration of nitrite ($NO_2$) which is a stable NO metabolite in media after adding the sample at each concentration to normal human umbilical vein endothelial cells (HUVEC). In the figure, A represents a control group, B represents a low-dose citrulline-added group (0.3 mM), C represents a serine-added group (0.3 mM), and D represents a low-dose citrulline and serine-added group. The data are expressed as mean±SEM (standard error), and N=3.

Although it is known that citrulline has an NO production activity, as shown in FIG. 1, in the low-dose citrulline+serine group in which the low-dose citrulline group which uses citrulline in the concentration range that does not affect NO production alone and the serine group were combined and added together, the NO level increased by about 32% as compared with that in the control group, and therefore, a remarkable effect of promoting NO production was observed. Further, as shown in FIG. 2, in the high-dose citrulline+serine group in which the high-dose citrulline group in which NO production was enhanced by citrulline alone and the serine group were combined and added together, the NO level increased by about 35% as compared with that in the control group, and therefore, a significant effect of promoting NO production was observed. This was a remarkable increase also as compared with that in the high-dose citrulline group. These results revealed that by using citrulline and serine in combination, the NO production activity is synergistically and effectively promoted without affecting the viability and proliferation ability of vascular endothelial cells, and thus, it was demonstrated that the agent of the present invention is an excellent agent for preventing or ameliorating vascular endothelial malfunction.

Examples of the present invention are described below.

Example 1

Production of Tablet Containing Citrulline and Serine

L-Citrulline (120 kg), L-serine (120 kg), cyclic oligosaccharide (19 kg), cellulose (57 kg), and pullulan (1 kg) were granulated using a fluidized-bed granulation dryer. The resulting granulated material is mixed with calcium stearate (3 kg) in a conical blender and compression molded in a rotary compression molding machine to produce tablets.

Example 2

Production of Enteric-Coated Tablet Containing Citrulline and Serine

The surfaces of the tablets produced in Example 1 are coated with a shellac solution to produce enteric-coated tablets.

Example 3

Production of Enteric-Coated Capsule Containing Citrulline and Serine

L-Citrulline (120 kg), L-serine (120 kg), cyclic oligosaccharide (19 kg), cellulose (57 kg), calcium stearate (3 kg), and pullulan (1 kg) are mixed in a conical blender. The resulting mixture (20 kg) is mixed and stirred with silicon dioxide (0.2 kg), and the resulting mixture is charged into a capsule filling machine to fill hard capsules with the mixture, whereby hard capsules are obtained. The surfaces of the obtained hard capsules are coated with a zein solution to produce enteric-coated capsules.

Example 4

Production of Drink Containing Citrulline and Serine (1)

L-Citrulline (1.28 kg), L-serine (1.28 kg), erythritol (3 kg), citric acid (0.05 kg), an artificial sweetener (3 g), and a flavor (0.06 kg) are stirred and dissolved in water (50 L) at a liquid temperature of 70° C. After being adjusted to pH 3.3 with citric acid, the solution is sterilized using a plate sterilizer and charged into a bottle, followed by sterilization with a pasteurizer to produce a drink.

Example 5

Production of Drink Containing Citrulline and Serine (2)

Citrulline (20 mg), L-serine (20 mg), and arginine (20 mg) are mixed with an appropriate amount of high fructose corn syrup, salt, citric acid, a flavor, sodium citrate, calcium lactate, iron pyrophosphate, calcium gluconate, potassium chloride, magnesium chloride, and a sweetener to produce a drink (555 ml).

Example 6

Production of Drink Containing Citrulline and Serine (3)

Citrulline (100 mg), L-serine (100 mg), arginine (100 mg), alanine (2.5 mg), glycine (2.5 mg), leucine (2.5 mg), isoleucine (1.3 mg), and valine (1.3 mg) are mixed with an appropriate amount of a flavor and a sweetener to produce a drink (300 ml).

Example 7

Production of Skin Toner Containing Citrulline and Serine

Ethanol (10.0% by weight), L-citrulline (2.0% by weight), L-serine (2.0% by weight), 1,3-butylene glycol (5.0% by weight), and purified water (83.0% by weight) are mixed to produce a skin toner.

Example 8

Production of Cream Containing Citrulline and Serine

Polyethylene glycol (PGE55), monostearate (2.00% by weight), self-emulsifying glyceryl monostearate (5.00% by weight), cetyl alcohol (4.00% by weight), squalane (6.00% by weight), 2-ethylhexanoic acid triglyceride (6.00% by weight), 1,3-butylene glycol (7.00% by weight), L-histidine (3.00% by weight), L-citrulline (1.00% by weight), L-serine (1.00% by weight), and purified water (66.00% by weight) are mixed to produce a cream.

Example 9

Production of Lotion Containing Citrulline and Serine

L-Citrulline (3.00% by weight), L-serine (3.00% by weight), L-serine (1.00% by weight), water-soluble collagen (1% aqueous solution; 1.00% by weight), sodium citrate (0.10% by weight), citric acid (0.05% by weight), licorice extract (0.20% by weight), 1,3-butylene glycol (3.00% by weight), and purified water (91.65% by weight) are mixed to produce a lotion.

Example 10

Production of Facial Mask Containing Citrulline and Serine

Polyvinyl alcohol (13.00% by weight), L-aspartic acid (1.00% by weight), L-citrulline (5.00% by weight), L-serine (5.00% by weight), lauroyl hydroxyproline (1.00% by weight), water-soluble collagen (1% aqueous solution; 2.00% by weight), 1,3-butylene glycol (3.00% by weight), ethanol (5.00% by weight), and purified water (70.00% by weight) are mixed to produce a facial mask.

Example 11

Production of Beauty Liquid Containing Citrulline and Serine

Hydroxyethyl cellulose (2% aqueous solution; 12.0% by weight), xanthan gum (2% aqueous solution; 2.0% by weight), L-citrulline (2.0% by weight), L-serine (2.0% by weight), 1,3-butylene glycol (6.0% by weight), concentrated glycerin (4.0% by weight), sodium hyaluronate (1% aqueous solution; 5.0% by weight), and purified water (69.0% by weight) are mixed to produce a beauty liquid.

The invention claimed is:

1. A method for enhancing nitrogen monoxide (NO) production in a subject, comprising a step of orally administering an effective amount of (a) citrulline or a salt thereof and (b) serine or a salt thereof, in a weight ratio of citrulline to serine of 1:1 to 10:1, to the subject, wherein the subject is a human with normal NO production and the subject is in need of enhanced NO production, thereby enhancing NO production in the subject.

2. The method of claim 1, wherein the citrulline is L-citrulline.

3. The method of claim 1, wherein the serine is L-serine.

4. The method of claim 1, wherein the citrulline is L-citrulline and the serine is L-serine.

5. The method of claim 1, wherein (a) the citrulline or a salt thereof and (b) the serine or a salt thereof are orally administered to the subject in a composition with a weight ratio of citrulline to serine of 1:1 to 10:1.

6. The method of claim 5, wherein the citrulline is L-citrulline and the serine is L-serine.

7. The method of claim 5, wherein the weight ratio of citrulline to serine in the composition is 1:1.

8. The method of claim 7, wherein the citrulline is L-citrulline and the serine is L-serine.

9. The method of claim 1, wherein the citrulline or salt thereof and serine or salt thereof are orally administered to the subject in a tablet, a powder, a granule, a pill, a suspension, an emulsion, an infusion/decoction, a capsule, a drink, a liquid, an elixir, an extract, a tincture, or a fluidextract.

10. A method for enhancing nitrogen monoxide (NO) production in a subject, comprising a step of orally administering an effective amount of (a) citrulline or a salt thereof and (b) serine or a salt thereof, in a weight ratio of citrulline to serine of 1:1 to 10:1, to the subject, wherein the subject is a human with normal NO production, thereby enhancing NO production in the subject.

11. The method of claim 10, wherein the citrulline is L-citrulline.

12. The method of claim 10, wherein the serine is L-serine.

13. The method of claim 10, wherein the citrulline is L-citrulline and the serine is L-serine.

14. The method of claim 10, wherein (a) the citrulline or a salt thereof and (b) the serine or a salt thereof are orally administered to the subject in a composition with a weight ratio of citrulline to serine of 1:1 to 10:1.

15. The method of claim 14, wherein the citrulline is L-citrulline and the serine is L-serine.

16. The method of claim 14, wherein the weight ratio of citrulline to serine in the composition is 1:1.

17. The method of claim 16, wherein the citrulline is L-citrulline and the serine is L-serine.

18. The method of claim 10, wherein the citrulline or salt thereof and serine or salt thereof are orally administered to the subject in a tablet, a powder, a granule, a pill, a suspension, an emulsion, an infusion/decoction, a capsule, a drink, a liquid, an elixir, an extract, a tincture, or a fluidextract.

* * * * *

UNITED STATES PATENT AND TRADEMARK OFFICE
CERTIFICATE OF CORRECTION

PATENT NO. : 9,833,426 B2
APPLICATION NO. : 14/411169
DATED : December 5, 2017
INVENTOR(S) : Masahiko Morita et al.

It is certified that error appears in the above-identified patent and that said Letters Patent is hereby corrected as shown below:

(72) Inventors:
"Miho Yin Komatsu, Tsukuka (JP)" should read "Miho Komatsu, Tsukuba (JP)"

Signed and Sealed this
Seventeenth Day of April, 2018

Andrei Iancu
*Director of the United States Patent and Trademark Office*